(12) United States Patent
Davis et al.

(10) Patent No.: US 9,936,988 B2
(45) Date of Patent: Apr. 10, 2018

(54) SURGICAL SYSTEM AND METHOD

(71) Applicant: Warsaw Orthopedic, Inc, Warsaw, IN (US)

(72) Inventors: Darren L. Davis, Arlington, TN (US); Eric C. Lange, Collierville, TX (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 63 days.

(21) Appl. No.: 15/090,694

(22) Filed: Apr. 5, 2016

(65) Prior Publication Data
US 2017/0281251 A1    Oct. 5, 2017

(51) Int. Cl.
*A61B 17/34*    (2006.01)
*A61B 17/70*    (2006.01)
*A61B 17/88*    (2006.01)
*A61B 17/00*    (2006.01)

(52) U.S. Cl.
CPC ...... *A61B 17/7097* (2013.01); *A61B 17/3468* (2013.01); *A61B 17/8816* (2013.01); *A61B 17/8841* (2013.01); *A61B 2017/00685* (2013.01); *A61B 2017/8838* (2013.01)

(58) Field of Classification Search
CPC ............ A61B 17/7097; A61B 17/3468; A61B 17/8816; A61B 17/8841; A61B 17/7065; A61B 17/7077; A61B 17/7062; A61B 2017/00685; A61B 2017/8838; A61B 2017/0256; A61B 2090/064; A61B 2090/061; A61B 2090/062; A61F 2/4611; A61F 2/4405; A61F 2/4657; A61F 2002/4658; A61F 2002/4662; A61F 2002/4666; A61F 2002/4687; A61F 2002/4627
USPC .................... 606/246–279, 86 A, 90, 96, 99; 623/17.11–17.16
See application file for complete search history.

(56) References Cited

U.S. PATENT DOCUMENTS

| | | | | |
|---|---|---|---|---|
| 7,582,106 | B2* | 9/2009 | Teitelbaum | A61B 17/1671 606/250 |
| 8,034,080 | B2* | 10/2011 | Malandain | A61B 17/025 606/249 |
| 8,317,831 | B2* | 11/2012 | Auyoung | A61B 17/7065 604/96.01 |
| 8,317,864 | B2* | 11/2012 | Kim | A61B 17/7065 606/248 |
| 9,603,714 | B2* | 3/2017 | Kitagawa | A61F 2/442 |
| 2011/0054532 | A1* | 3/2011 | De Moura | A61B 17/7065 606/249 |

* cited by examiner

Primary Examiner — Pedro Philogene

(57) ABSTRACT

A surgical instrument includes a body having an actuator and being connectable with a pressurized fluid source. A first member is connected with the body and the fluid source. The first member is configured for connection with an implant disposable between a contracted configuration and an expanded configuration. A second member defines a cavity configured for disposal of the first member and the expandable implant. The second member is connected with the actuator for selective translation relative to the first member to position the implant in the contracted configuration. Systems, implants and methods are disclosed.

20 Claims, 10 Drawing Sheets

SURGICAL SYSTEM AND METHOD

TECHNICAL FIELD

The present disclosure generally relates to medical devices for the treatment of musculoskeletal disorders, and more particularly to a surgical system that includes one or more surgical instruments and method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes decompression, discectomy, laminectomy, laminoplasty, fusion, fixation and implantable prosthetics. For example, spinal stabilization treatments may employ implants, which may include interbody devices, plates and bone fasteners to stabilize vertebrae and facilitate healing. This disclosure describes an improvement over these technologies.

SUMMARY

In one embodiment, a surgical instrument is provided. The surgical instrument includes a body having an actuator and is connectable with a pressurized fluid source. A first member is connected with the body and the fluid source. The first member is configured for connection with an implant disposable between a contracted configuration and an expanded configuration. A second member defines a cavity configured for disposal of the first member and the expandable implant. The second member is connected with the actuator for selective translation relative to the first member to position the implant in the contracted configuration. In some embodiments, systems, implants and methods are provided.

BRIEF DESCRIPTION OF THE DRAWINGS

The present disclosure will become more readily apparent from the specific description accompanied by the following drawings, in which.

Figure 1:
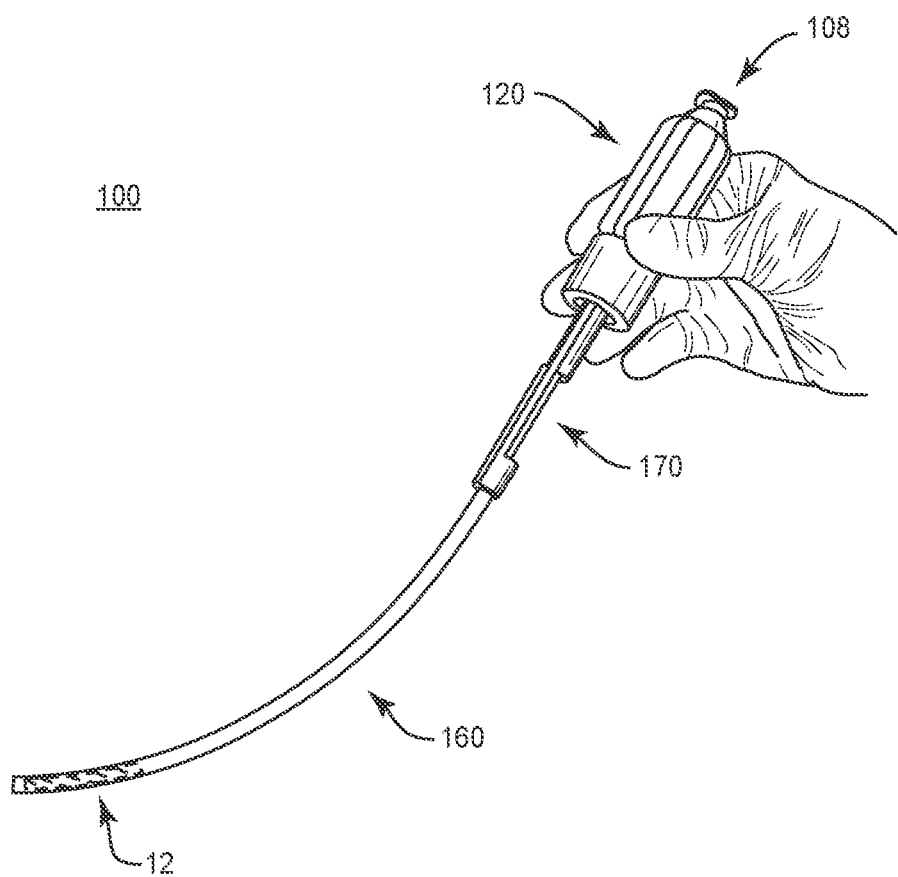
FIG. 1 is a perspective view of components of one embodiment of a surgical system in accordance with the principles of the present disclosure.
Figure 3:
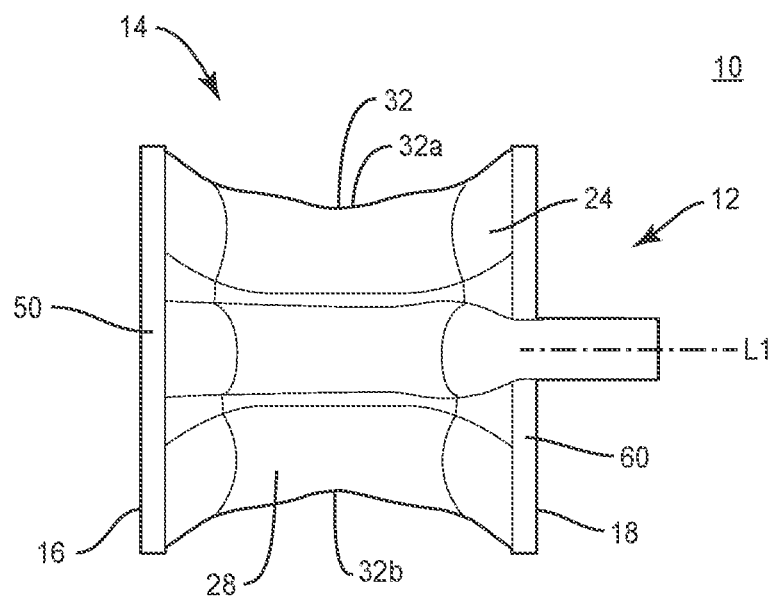
Figure 4:
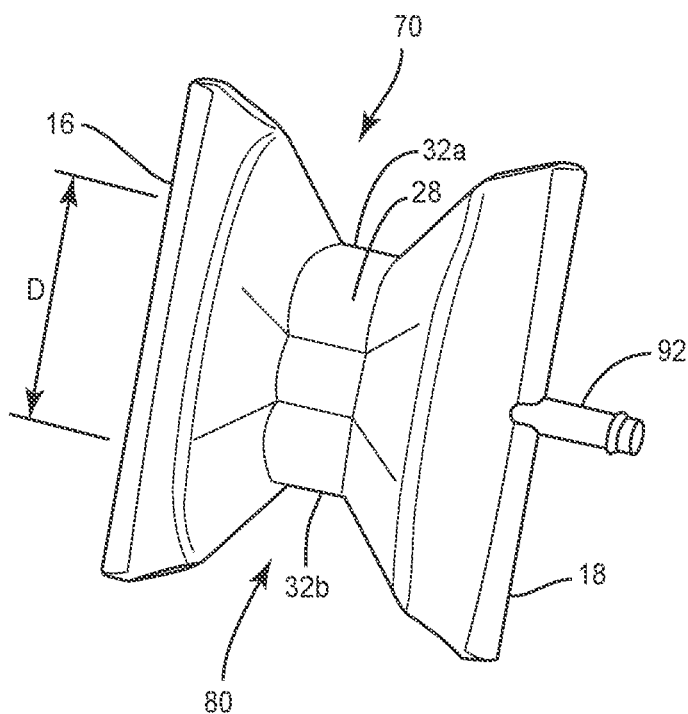
Figure 5:
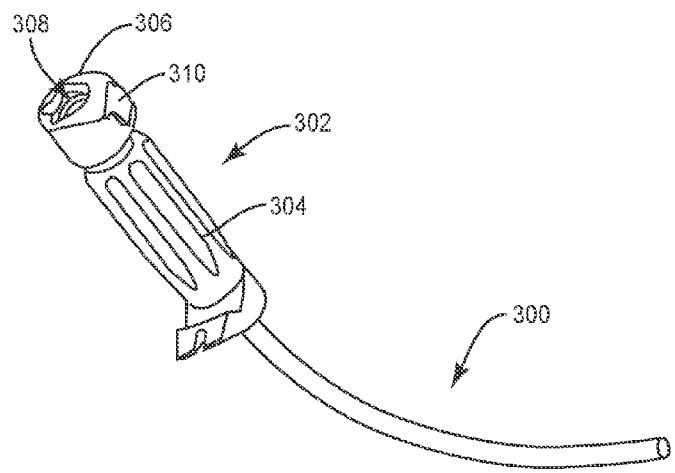
Figure 6:
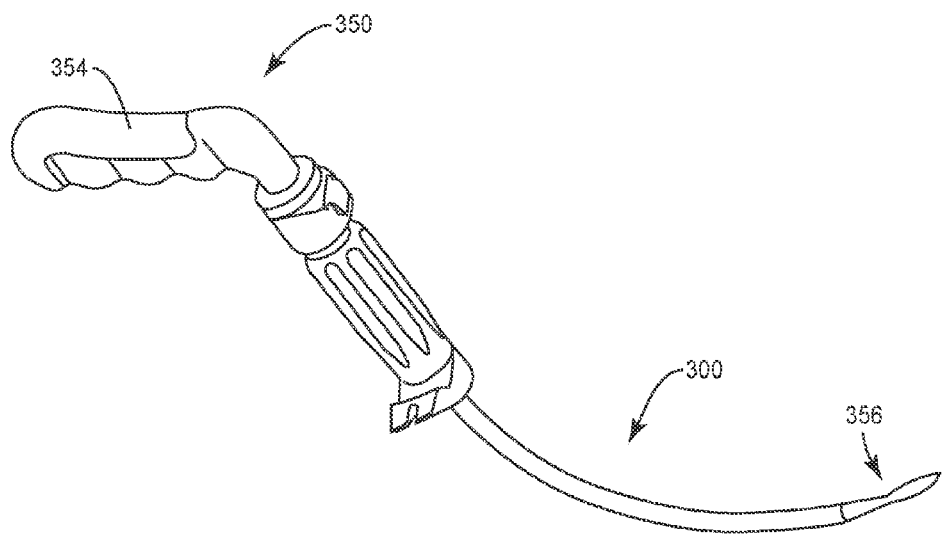
Figure 7:
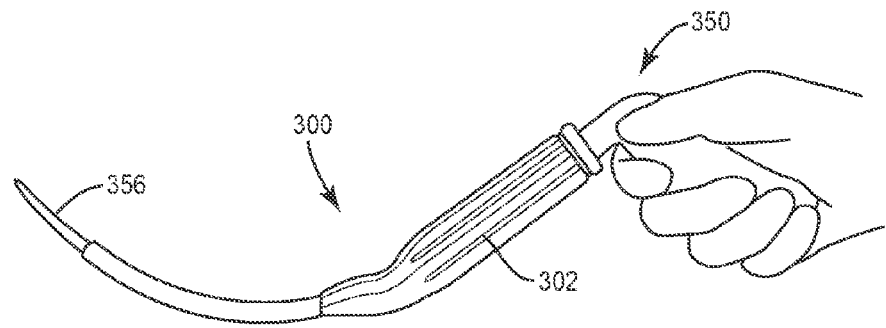
Figure 8:
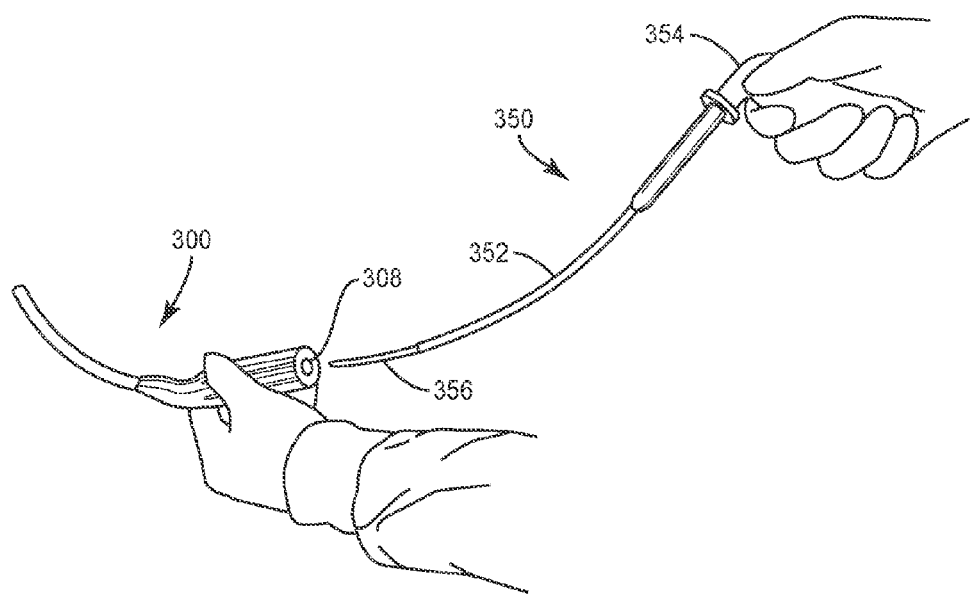
Figure 9:
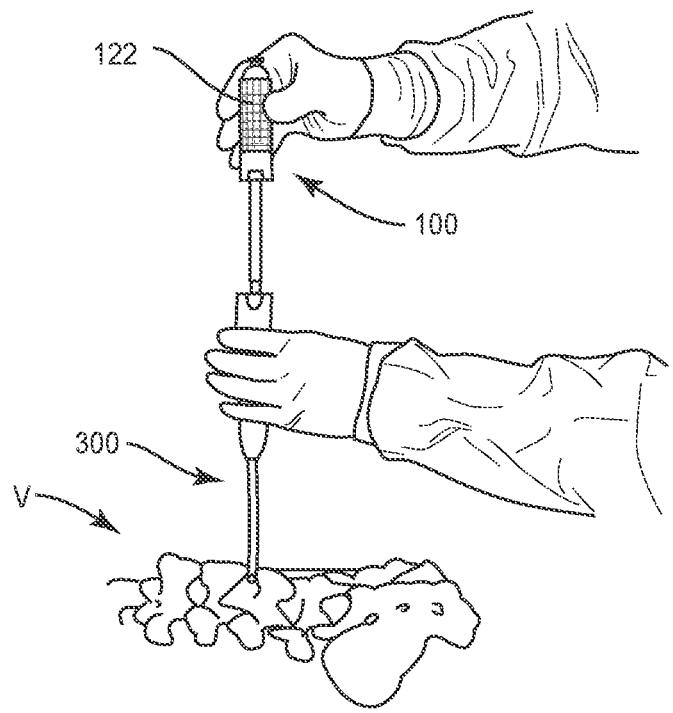
Figure 10:
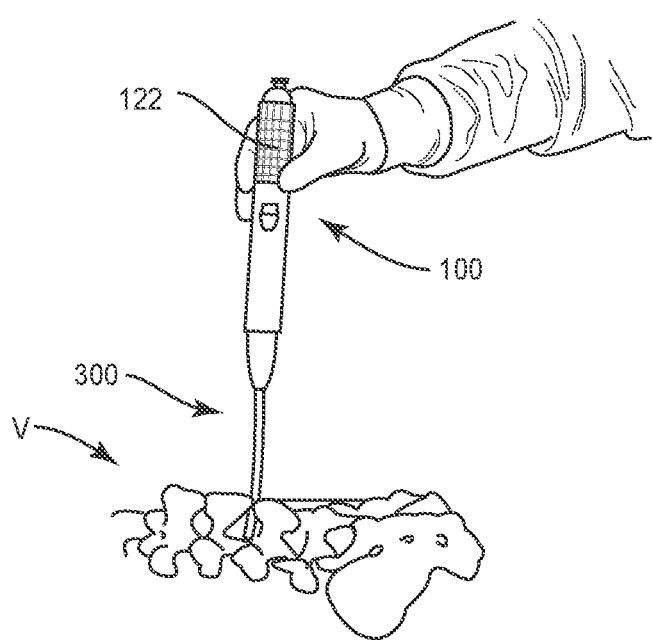
Figure 11:
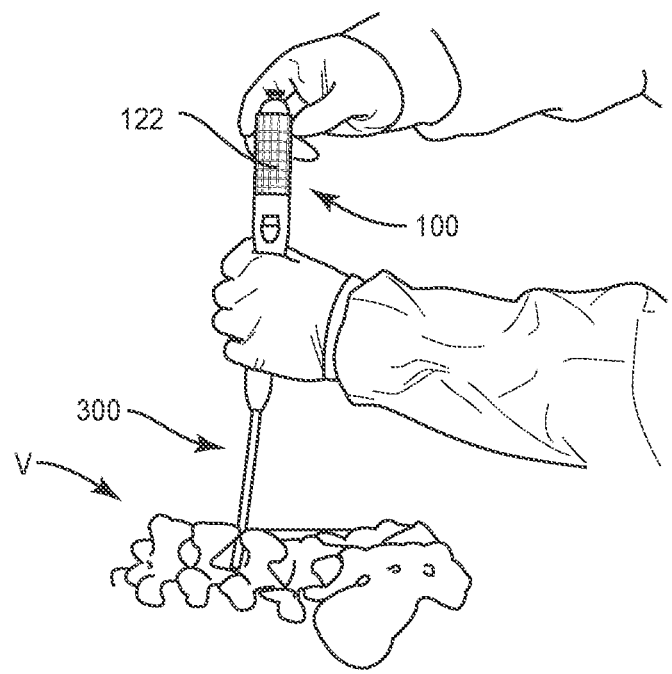
Figure 12:
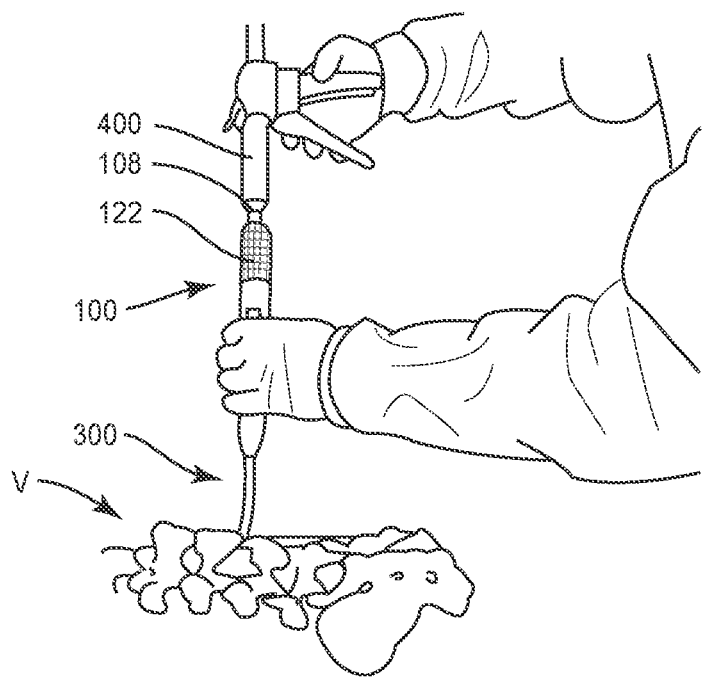
Figure 13:
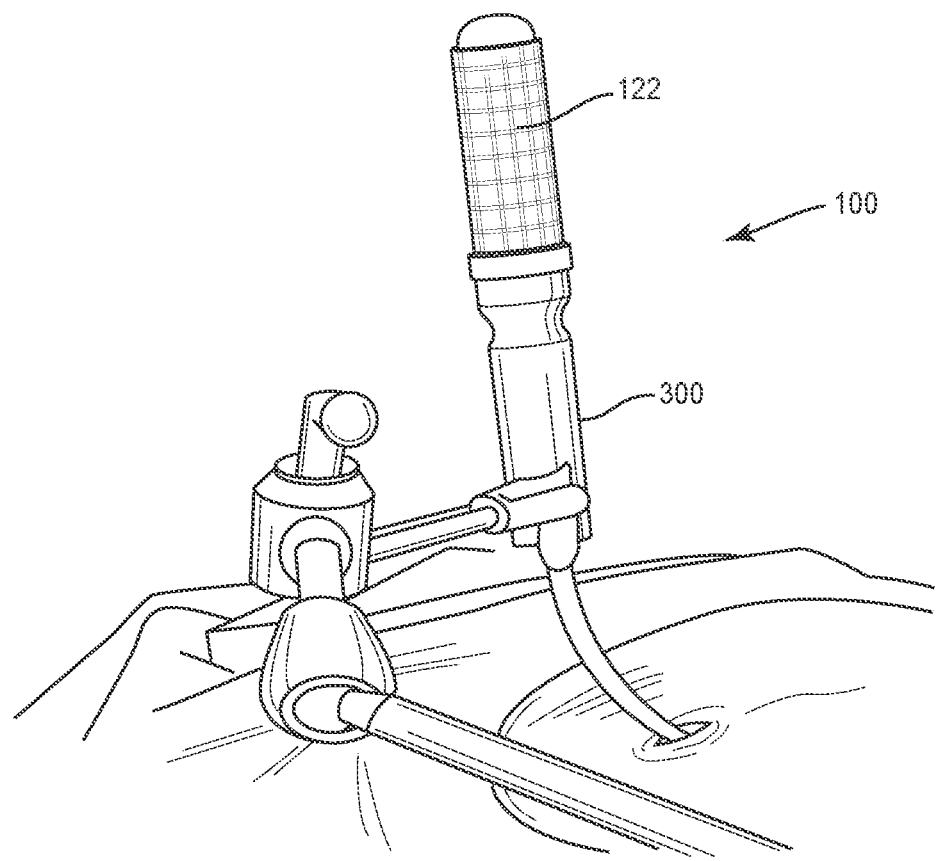
Figure 14:
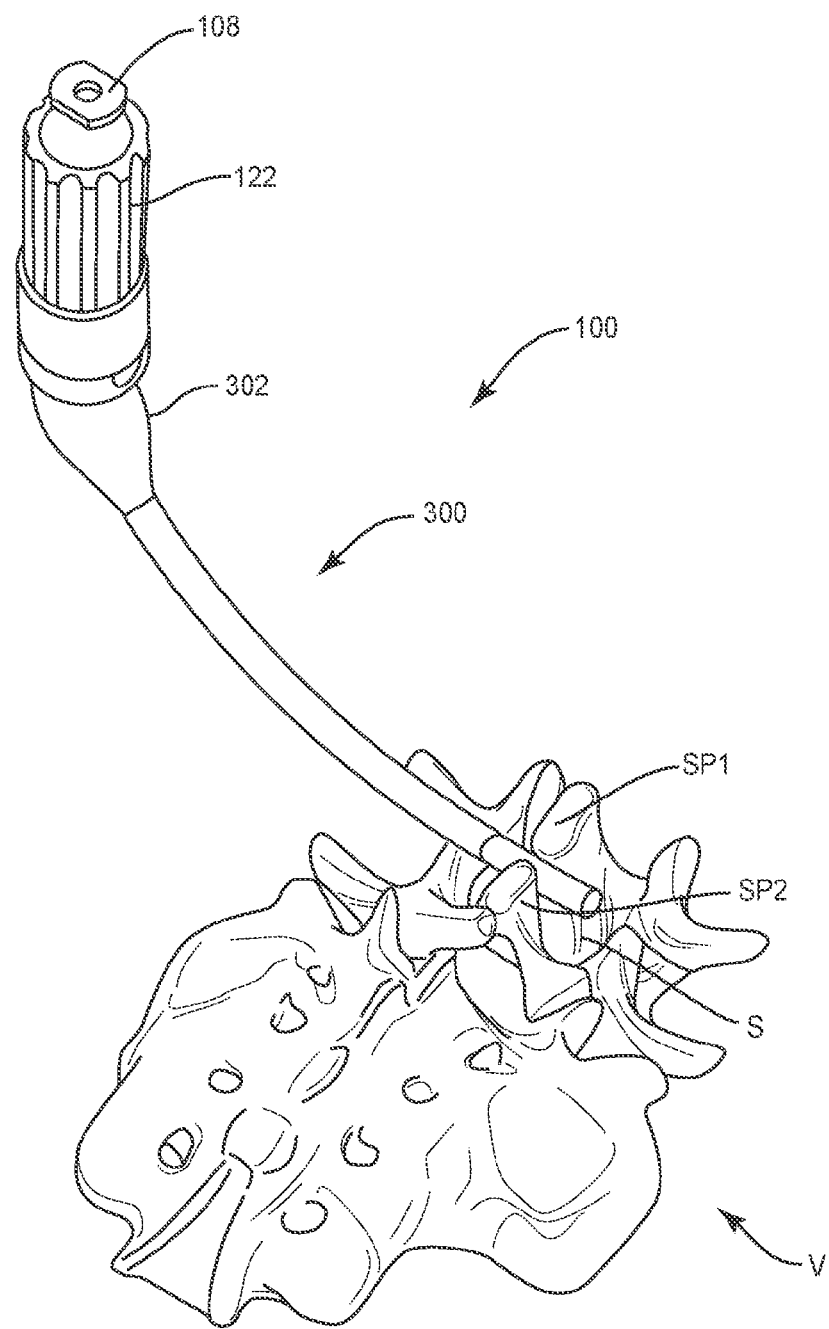
Figure 15:
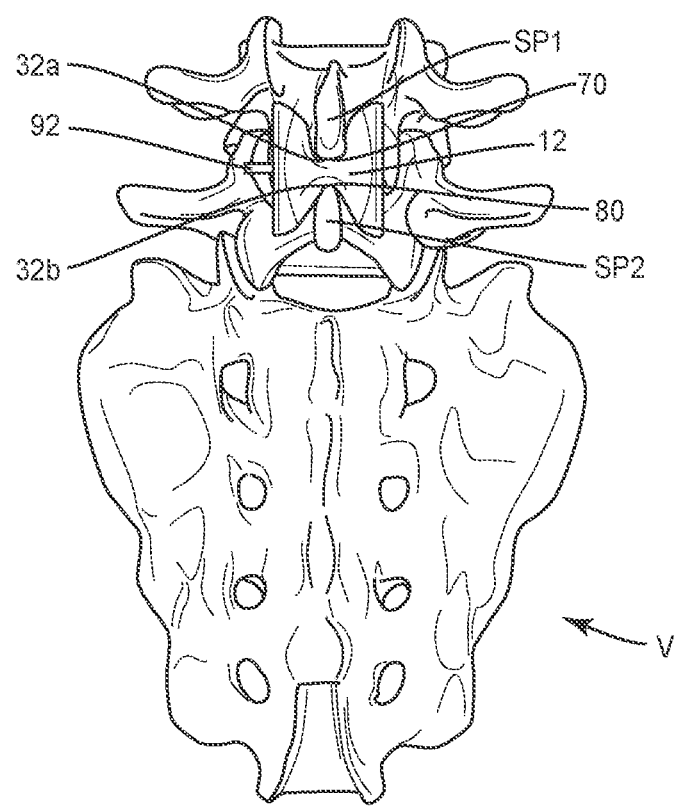

FIG, 2 is a cross section view of the components shown in FIG. 1;

FIG. 3 is a side view of components of one embodiment of a surgical system in accordance with the principles of the present disclosure;

FIG. 4 is a perspective view of the components shown in FIG. 3;

FIG, 5 is a perspective view of components of one embodiment of a surgical system in accordance with the principles of the present disclosure;

FIG. 6 is a perspective view of components of one embodiment of a surgical system in accordance with the principles of the present disclosure;

FIG. 7 is a perspective view of components of one embodiment of a surgical system in accordance with the principles of the present disclosure;

FIG. 8 is a perspective view, with parts separated, of components of one embodiment of a surgical system in accordance with the principles of the present disclosure;

FIG. 9 is an perspective view of components of one embodiment of a surgical system in accordance with the principles of the present disclosure disposed with vertebrae;

FIG. 10 is an perspective view of components of one embodiment of a surgical system in accordance with the principles of the present disclosure disposed with vertebrae;

FIG. 11 is an perspective view of components of one embodiment of a surgical system in accordance with the principles of the present disclosure disposed with vertebrae;

FIG. 12 is an perspective view of components of one embodiment of a surgical system in accordance with the principles of the present disclosure disposed with vertebrae;

FIG. 13 is an perspective view of components of one embodiment of a surgical system in accordance with the principles of the present disclosure disposed with a patient body;

FIG. 14 is an perspective view of components of one embodiment of a surgical system in accordance with the principles of the present disclosure disposed with vertebrae; and FIG. 15 is a plan view of components of one embodiment of a surgical system in accordance with the principles of the present disclosure disposed with vertebrae.

DETAILED DESCRIPTION

The exemplary embodiments of the surgical system and related methods of use disclosed are discussed in terms of medical devices for the treatment of musculoskeletal disorders and more particularly, in terms of a surgical system including a spinal implant and a method for treating a spine. In some embodiments, the systems and methods of the present disclosure are employed with a spinal joint fusion, for example, with a cervical, thoracic, lumbar and/or sacral region of a spine. In some embodiments, the spinal implant includes an interbody device, expandable implant and/or bone fasteners. In some embodiments, the systems and methods of the present disclosure are employed with decompression, discectomy, laminectomy, laminoplasty, fusion, fixation and implantable prosthetic procedures.

In some embodiments, the surgical system includes a surgical instrument configured to facilitate an injectable interspinous process delivery. In some embodiments, the surgical instrument is configured for use with a minimal access surgical technique (MAST) for insertion, inflation and deployment of an implant. In some embodiments, the implant is configured to be filled with a flowable substance that can be cured in-vivo. In some embodiments, the surgical instrument includes a curved access cannula and a removable trocar. In some embodiments, the surgical instrument is configured to facilitate delivery with controlled implant positioning and deployment. In some embodiments, the surgical instrument includes an integrated in-line mixer. In some embodiments, the surgical instrument includes transfer tubing. In some embodiments, the surgical instrument includes a detachable in-vivo implant filling connector. In some embodiments, the surgical instrument facilitates a two part curable flowable material for filling an implant in-vivo.

In some embodiments, the access cannula is configured with a curved end to facilitate dorsal entry to position an access tip between tissue, such as, for example, spinous processes. In some embodiments, the trocar is configured for removal from the access cannula to allow subsequent insertion of an implant inserter. In some embodiments, the trocar includes a flexible shaft disposed between a handle and a rigid trocar tip. In some embodiments, the flexible shaft is configured to facilitate translation along a linear portion of the access cannula handle.

In some embodiments, the surgical instrument is configured for connection with image guidance to produce radiographic images to facilitate positioning of the trocar tip. In some embodiments, after positioning the trocar tip, the access cannula is attached to a surgical table and the trocar is removed. In some embodiments, attachment to the surgical table facilitates docking of the surgical instrument with the access cannula handle when the trocar tip is removed and resists and/or prevents movement relative to an anatomical orientation.

In some embodiments, the surgical instrument includes an implant delivery instrument having an injector attached. In some embodiments, the surgical instrument includes an implant delivery instrument having an outer tube configured for rotation and retraction. In some embodiments, the surgical instrument includes an implant delivery instrument configured for pre-assembly with an implant. In some embodiments, the surgical instrument includes an implant delivery instrument having a fill tube. In some embodiments, the surgical instrument includes an implant delivery instrument having outer tubing configured for retraction. In some embodiments, the surgical instrument includes an implant delivery instrument having a handle configured for attachment with an access cannula. In some embodiments, the surgical instrument includes a cavity configured for disposal of an implant. In some embodiments, the implant is folded within the cavity. In some embodiments, the surgical instrument includes an implant delivery instrument having a fill tube configured for connection with the implant, In some embodiments, the surgical instrument includes an implant delivery instrument having a threaded handle configured to retract the outer cannula to facilitate deployment of the implant. In some embodiments, the surgical instrument includes an implant delivery instrument having a transfer tube configured for disposal of a static material mixer. In some embodiments, the surgical instrument includes an implant delivery instrument having an attachment port configured for injection in-vivo of a curable flexible material. In some embodiments, the surgical instrument includes an implant delivery instrument configured for attachment with an injection device to inflate the implant with flowable material.

In some embodiments, the surgical instrument includes an implant delivery instrument having an integrated in-line mixer, transfer tubing and a detachable in-vivo implant filling connector. In some embodiments, the surgical instrument includes an implant delivery instrument configured to fill the implant during release of the implant, incrementally or at final deployment. In some embodiments, the surgical instrument includes an implant delivery instrument having indication marks on the handle to provide a reference of position during implant deployment. In some embodiments, the surgical instrument includes an implant delivery instrument having a filling tube connected to the implant connector. In some embodiments, the surgical instrument includes an implant delivery instrument configured to evacuate air trapped within the implant delivery instrument during pre-implant injection as the flowable material passes through a gas/liquid check valve. In some embodiments, the flowable material is configured to flow between the access and outer cannula proximally towards a back of the access cannula handle. In some embodiments, the surgical instrument includes an implant delivery instrument having a male/female connection configured to release the implant delivery instrument. After retraction, the outer cannula is disposed in a final fully retracted position.

In some embodiments, the surgical instrument includes an implant delivery instrument configured for insertion through the access cannula to position the implant within patient anatomy. In some embodiments, the surgical instrument includes an implant delivery instrument having a rotatable handle configured to facilitate controlled deployment of the implant that is captured within an end of the outer cannula. In some embodiments, the implant is pre-packed within the outer cannula in an orientation for deployment.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or spinal implants, such as, for example, an expandable implant at a surgical site within a body of a patient, which includes, for example, vertebrae. One or more of the components of spinal implant system 10 including an expandable implant can be employed, for example, in decompression, discectomy, laminectomy, laminoplasty, fusion, fixation and implantable prosthetic procedures to treat patients suffering from a spinal disorder to provide stabilization and decompression. In some embodiments, one or more of the components of spinal implant system 10 is employed with a method for implanting an interspinous process spacer between two adjacent vertebrae, which includes introducing the interspinous spacer adjacent a superior spinous process and an inferior spinous process.

Figure 2:
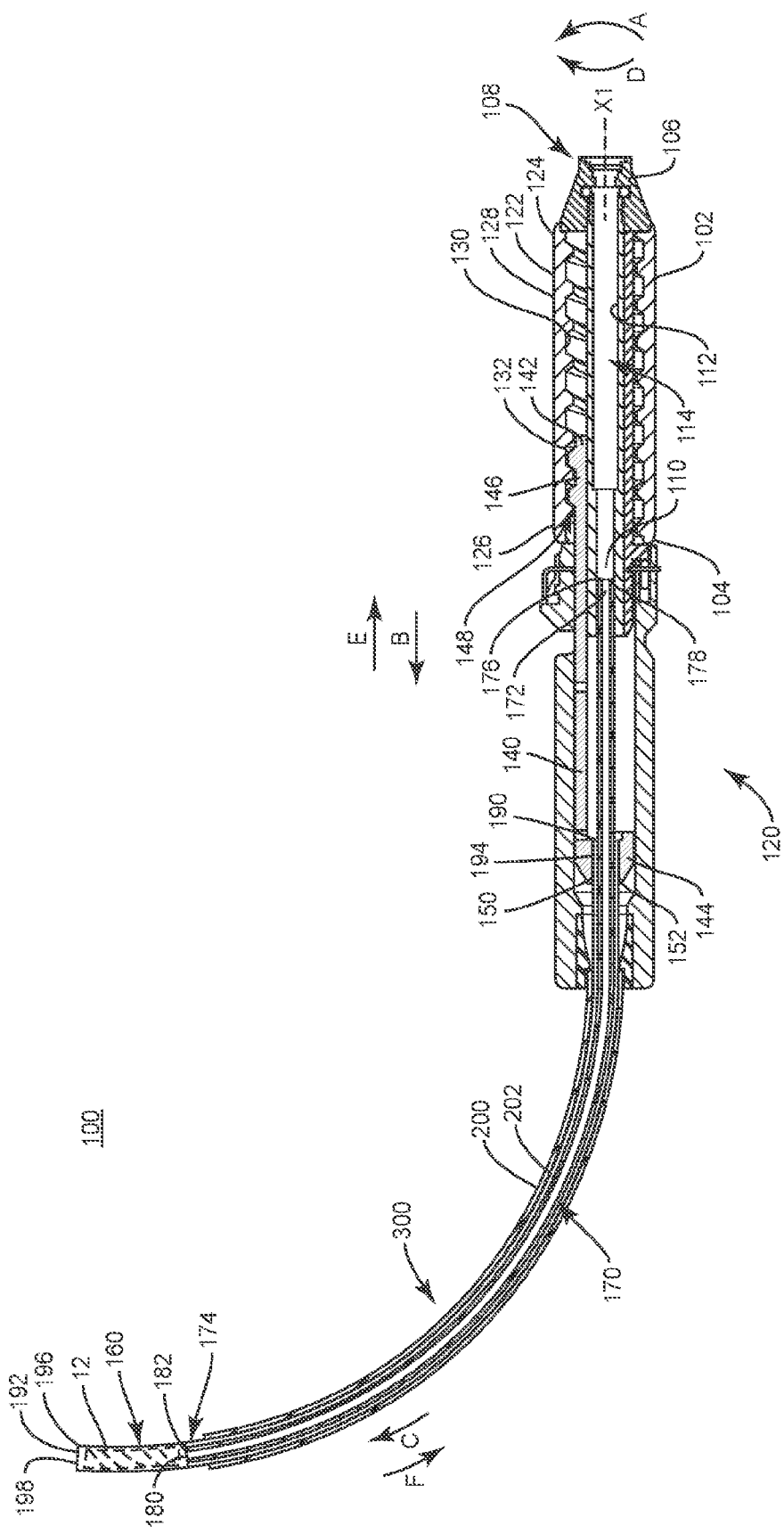

Spinal implant system 10 includes a spinal implant, such as, for example, an expandable implant 12. Expandable implant 12 includes a body 14. Body 14 extends between an end 16 and an end 18, and defines a longitudinal axis L1. Body 14 is configured for disposal between a contracted configuration, as shown in FIGS. 1 and 2, to facilitate insertion with a delivery and/or insertion device or passageway, and an in vivo expandable configuration, as shown in FIGS. 3 and 4 and described herein. In some embodiments, an overall geometry of body 14, in a contracted or expanded configuration, may have various configurations, such as, for example, oval, oblong, triangular, rectangular, square, polygonal, irregular, uniform, non-uniform, variable and/or tapered. In some embodiments, a thickness defined by body 14 may be uniformly increasing or decreasing, or have alternate diameter dimensions along its length. In some embodiments, body 14 can have a uniform thickness/diameter.

Body 14 includes an inner surface (not shown) and an outer surface 24 that extend between ends 16, 18. The inner surface defines a cavity that is configured to receive an injectable material during expansion. Body 14 includes an intermediate portion 28. In some embodiments, intermediate portion 28 includes a baffle to restrict and/or regulate the flow of the injectable material and provide an expansion limit surface of body 14. In some embodiments, the baffle is configured to restrain and/or limit expansion of body 14 adjacent intermediate portion 28 during injection of a material as body 14 is filled, as described herein. In some embodiments, intermediate portion 28 includes an expansion limit surface 32 that extends about intermediate portion 28 and includes surfaces 32a, 32b configured to engage tissue, as described herein. In some embodiments, expansion limit surface 32 is restricted with the baffle to reduce a dimension D of intermediate portion 28, as shown in FIG. 4. In some embodiments, the baffle is configured to regulate expansion of dimension D to a specific size and/or configuration to facilitate distraction in the cranial-caudal direction of a patient body. In some embodiments, the baffle is configured to limit expansion of dimension D in one or more directions, such as, for example, an anterior direction and a posterior direction. In some embodiments, limited expansion of intermediate portion 28 resists and/or prevents expansion of intermediate portion 28 into a spinal canal of the patient body avoiding impingement of the spinal canal.

Intermediate portion 28 is tapered and/or extends in an angled orientation to a portion 50 of end 16 and a portion 60 of end 18. In some embodiments, portion 50 and/or portion 60 have a non-baffled configuration and can be expandable to a selected configuration to engage selected tissue. In some embodiments, portion 50 and/or portion 60 are configured for expansion as a material is injected into body 14, as described herein, to the structural limits of portion 50 and/or portion 60 and/or tissue engaged therewith. Expansion of portion 50 and/or portion 60 provide directional stability to body 14 during expansion.

In some embodiments, body 14 is expandable such that surface 24 defines a superior cavity 70 for disposal of vertebrae, such as, for example, a spinous process, as described herein, In some embodiments, body 14 is expandable such that surface 24 defines an inferior cavity 80 for disposal of vertebrae, such as, for example, a spinous process, as described herein. In some embodiments, body 14 is manufactured from a porous fabric material. In some embodiments, surface 24 is coated with a non-permeable material to coat the porous material. In some embodiments, the non-permeable material is configured to prevent leakage of a material injected with body 14. In some embodiments, the non-permeable material includes an antimicrobial coating. In some embodiments, the non-permeable material includes a silicone coating. In some embodiments, surface 24 is pre-coated. In some embodiments, surface 24 is dipped in a non-permeable material. In some embodiments, surface 24 is sprayed with a non-permeable material. Body 14 includes a tubular filling port 92 disposed with end 18 and includes a plastic connector configured for connection with a source of injectable material, A material is injected through port 92 into body 14 for expansion of body 14 in vivo.

Body 14 is configured for disposal between a contracted configuration and an in vivo expandable configuration, as described herein. In the contracted configuration, body 14 is evacuated and ends 16, 18 and intermediate portion 28 are manipulated and/or folded into a configuration to facilitate insertion of body 14 with a delivery device, such as, for example, a surgical instrument 100, as described herein, for disposal of expandable implant 12 at a surgical site. Upon disposal of body 14 with a selected location at a surgical site, surgical instrument 100 provides a pathway for injecting a material into the cavity to inflate body 14 to an expanded configuration. See also, the examples and disclosure of systems, implants and methods shown and described in U.S. patent application Ser. No. 15/090,667 filed Apr. 5, 2016, the entire contents of which being incorporated herein by reference.

Spinal implant system 10 includes a surgical instrument 100 having a body 102, as shown in FIGS. 1 and 2. Body 102 extends between an end 104 and an end 106 and defines an axis X1. End 106 includes a port 108 configured for connection with a pressurized fluid source configured to supply an injectable material, as described herein. In some embodiments, the fluid source is detachably connected with port 108. In some embodiments, port 108 includes a pressure fit, friction fit, luer lock or threaded connection for connecting with the fluid source. In some embodiments, port 108 is integrally connected or monolithically formed with the fluid source.

End 104 includes an opening 110 configured for passage of an injectable material, as described herein. Body 102 includes a surface 112 that defines a cavity, such as, for example, a mixing chamber 114. Chamber 114 is disposed in axial alignment with axis X1. In some embodiments, chamber 114 may be disposed at alternate orientations relative to axis X1, such as, for example, transverse and/or other angular orientations, such as, acute or obtuse. Chamber 114 is disposed in a fluid communication with port 108. Chamber 114 is configured to receive the injectable material prior to injection into expandable implant 12, as described herein, and in some embodiments, can be employed to mix one or more materials, as described herein.

Body 102 includes an actuator 120. Actuator 120 includes a part, such as, for example, a rotatable handle 122. Handle 122 extends between an end 124 and an end 126 along axis X1 In some embodiments, handle 122 may be disposed at alternate orientations relative to axis X1, such as, for example, transverse and/or other angular orientations, such as, acute or obtuse. Handle 122 includes a surface 128 configured as a gripping surface configured to facilitate manipulation of handle 122. Handle 122 includes a surface 130. In some embodiments, surface 130 includes a threaded portion 132. Portion 132 is configured for rotatable engagement with a portion of a part, such as, for example, a tubular screw 140, as described herein. Rotation of handle 122 is configured to selectively translate a member, such as, for example, an outer cannula 160 to selectively position expandable implant 12, as described herein.

Actuator 120 includes tubular screw 140. Screw 140 extends between an end 142 and an end 144 and extends along axis X1. In some embodiments, screw 140 may be disposed at alternate orientations relative to axis X1, such as, for example, transverse and/or other angular orientations, such as, acute or obtuse. End 142 includes a surface 146 configured for engagement with portion 132. In some embodiments, surface 146 includes a threaded portion 148 configured for a threaded engagement with portion 132. End 144 includes a surface 150 that defines a cavity 152. Cavity 152 is configured for engagement with cannula 160. Rotation of handle 122 is configured to translate screw 140 to selectively dispose cannula 160 in a selected orientation to position and/or expose expandable implant 12 for deployment.

Surgical instrument 100 includes a member, such as, for example, a filling tube 170. Tube 170 extends between an end 172 and an end 174. End 172 includes a surface 176 that defines an opening 178. Surface 176 is configured for engagement with opening 110 of body 102. In some embodiments, surface 176 includes a pressure fit, friction fit or threaded connection for connecting with the surface of opening 110. In some embodiments, tube 170 is integrally connected or monolithically formed with body 102. Tube 170 is flexible to facilitate manipulation through cannula 160, as described herein, to facilitate connection with expandable implant 12. Connection of tube 170 with opening 110 facilitates the flow of the injectable material from chamber 114, through opening 110 and into tube 170.

End 174 includes a surface 180 that defines an opening 182. Surface 180 is configured for connection with port 92 to inject an injectable material into expandable implant 12, as described herein. In some embodiments, surface 180 includes a pressure fit, friction fit or threaded connection for connecting with port 92. In some embodiments, tube 170 is integrally connected or monolithically formed with port 92.

Cannula 160 extends between an end 190 and an end 192. End 190 includes a surface 194 configured for disposal with cavity 152. In some embodiments, surface 194 includes a pressure fit, friction fit or threaded connection for connecting with surface 150 of cavity 152. In some embodiments, cannula 160 is integrally connected or monolithically formed with screw 140.

End 192 includes a surface 196 that defines a cavity 198. Cavity 198 is configured for disposal of expandable implant 12 in the contracted configuration during insertion to the surgical site. In some embodiments, expandable implant 12 is folded in the contracted configuration such that surface 196 compresses and captures expandable implant 12 within cavity 198 and contains expandable implant 12 within cannula 160. Cannula 160 includes a surface 200 that defines a cavity, such as, for example, a channel 202. Channel 202 is configured for disposal of tube 170.

For example, rotation of handle 122 in a counterclockwise direction, as shown by arrow A in FIG. 2, causes portions 132, 148 to threadably engage such that handle 122 and screw 140 are driven apart. As such, screw 140 translates relative to handle 122 in a distal direction, as shown by arrow B in FIG. 2. Translation of screw 140 in the distal direction causes translation of cannula 160 adjacent end 174 in an axial direction, as shown by arrow C in FIG. 2. Translation of cannula 160 disposes cannula 160 in a configuration to contain expandable implant 12 in a folded configuration within cavity 198. Containment of expandable implant 12 within cavity 198 and cannula 160 facilitates insertion of expandable implant 12 to a surgical site.

Rotation of handle 122 in a clockwise direction, as shown by arrow D in FIG. 2, causes portions 132, 148 to threadably engage such that handle 122 and screw 140 are drawn together. As such, screw 140 translates relative to handle 122 in a proximal direction, as shown by arrow E in FIG. 2. Translation of screw 140 in the proximal direction causes translation of cannula 160 adjacent end 174 in an opposing axial direction, as shown by arrow F in FIG. 2. Translation of cannula 160 in the opposing axial direction retracts cannula 160 relative to tube 170 to facilitate selective positioning and exposure of expandable implant 12. Retraction of cannula 160 relative to tube 170 facilitates deployment of expandable implant 12 at a surgical site and/or expansion of implant 12 between a contracted configuration and an expanded configuration. Cannula 160 can be selectively manipulated to facilitate a range of movement of cannula 160 relative to expandable implant 12 to position and orient expandable implant 12 in situ.

A source of pressurized fluid is connected with port 108 and injected in vivo through tube 170 into body 14 to inflate body 14. Body 14 is expandable in vivo to a selected expanded configuration such that surface 24 defines cavity 70 and cavity 80 for engagement with selected tissue surfaces, as described herein, In some embodiments, surface 24 is engageable with the selected tissue surfaces to resist and/or prevent undesirable movement or displacement of body 14 from the selected tissue surfaces, as described herein, In some embodiments, the injectable material is a biocompatible fluid, as described herein. In some embodiments, the injectable material includes silicone configured for injection in an initial liquid state and cured to a relatively solid state in vivo.

In some embodiments, spinal implant system 10 includes a surgical instrument, such as, for example, an access cannula 300, as shown in FIGS. 5-8. In some embodiments, cannula 300 can be integrally formed with surgical instrument 100. In some embodiments, cannula 300 includes a curved configuration to facilitate a dorsal insertion and positioning of an access tip of cannula 300 between tissue. In some embodiments, cannula 300 includes a linear configuration. Cannula 300 includes a handle 302. Handle 302 includes a surface 304 that defines a gripping surface configured to facilitate manipulation of cannula 300, Cannula 300 includes a surface 306 that defines a cavity, such as, for example, a channel 308. Channel 308 is configured for movable disposal of surgical instruments, such as, for example, surgical instrument 100 and a trocar 350, as described herein. In some embodiments, handle 302 includes a locking mechanism 310 configured to releasably fix a selected surgical instrument with cannula 300. In some embodiments, locking mechanism 310 includes, such as, for example, a biasing member, spring hinge, clip, nail, rivet and/or adhesive to releasably fix a selected surgical instrument with cannula 300.

In some embodiments, trocar 350 includes a flexible shaft 352, as shown in FIG. 8. In some embodiments, shaft 352 is disposed between a handle 354 and a rigid tip 356. In some embodiments, shaft 352 is flexible to facilitate translation through a linear section of cannula 300.

In assembly, operation and use, spinal implant system 10, similar to the systems and methods described herein, is employed to treat a selected section of vertebrae V, as shown in FIGS. 9-15. A medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating a spine disorder. In some embodiments, one or all of the components of spinal implant system 10 can be delivered or implanted as a pre-assembled device or can be assembled in situ. The components of spinal implant system 10 may be completely or partially revised, removed or replaced.

An incision is made in the body of a patient and a cutting instrument, which can include trocar 350, as shown in FIGS. 6-8, creates a surgical pathway for implantation of components of spinal implant system 10 with a portion of vertebrae V including spinous process SP1 and spinous process SP2, as shown in FIGS. 14 and 15. A preparation instrument (not shown) can be employed to prepare tissue surfaces of vertebrae V and a space S between spinous process SP1 and spinous process SP2, as well as for aspiration and irrigation of a surgical region.

In some embodiments, cannula 300 is translated over trocar 350, as shown in FIGS. 7 and 8, and delivered via the surgical pathway for insertion adjacent the surgical site including spinous process SP1 and spinous process SP2, In some embodiments, the curved configuration of cannula 300 facilitates a dorsal insertion and positioning of an access tip of cannula 300 between spinous process SP1 and spinous process SP2, as shown in FIGS. 13 and 14. In some embodiments, trocar 350 is removed from cannula 300 to facilitate subsequent entry of surgical instrument 100 including expandable implant 12, as described herein, through cannula 300. In some embodiments, cannula 300 is attached with a surgical table, as shown in FIG. 13.

Body 14 is evacuated and, ends 16, 18 and intermediate portion 28, are manipulated and/or folded into a contracted configuration for disposal of body 14 with cannula 160. Handle 122 is rotated in a counterclockwise direction, as shown by arrow A in FIG. 2, causing portions 132, 148 to threadably engage driving handle 122 and screw 140 apart. Screw 140 translates relative to handle 122 in a distal direction, as shown by arrow B in FIG. 2. Translation of screw 140 in the distal direction causes translation of cannula 160 adjacent end 174 in an axial direction, as shown by arrow C in FIG. 2. Cannula 160 is translated to contain expandable implant 12 in the folded configuration within cavity 198. Surgical instrument 100 including expandable implant 12 is manipulated such that cannula 160 is delivered via the surgical pathway for insertion adjacent the surgical site. Cannula 160 with implant 12 is disposed with space S between spinous process SP1 and spinous process SP2.

Handle 122 is rotated in a clockwise direction, as shown by arrow D in FIG. 2, causing portions 132, 148 to threadably engage drawing handle 122 and screw 140 together. Screw 140 translates relative to handle 122 in a proximal direction, as shown by arrow E in FIG. 2. Translation of screw 140 in the proximal direction causes translation of cannula 160 adjacent end 174 in an opposing axial direction, as shown by arrow F in FIG. 2. Translation of cannula 160 in the opposing axial direction retracts cannula 160 relative to tube 170 to selectively position and expose expandable implant 12 adjacent space S between spinous process SP1 and spinous process SP2. Retraction of cannula 160 relative to tube 170 disposes expandable implant 12 at the surgical site for deployment and/or expansion. Expandable implant 12 is positioned between spinous process SP1 and spinous process SP2 such that surface 32a is oriented to engage spinous process SP1 and surface 32b is oriented to engage spinous process SP2, as shown in FIGS. 14 and 15.

A source of pressurized injectable material, such as, for example, injector system 400 is attached with surgical instrument 100, as shown in FIG. 12. Injector system 400 is connected with port 108 and injects silicone in vivo with implant 12. Silicone is injected through chamber 114 and tube 170, into body 14 in vivo to expand and/or inflate body 14. In some embodiments, silicone can be injected during deployment of expandable implant 12 from surgical instrument 100. In some embodiments, silicone can be injected incrementally. In some embodiments, air trapped within surgical instrument 100 is evacuated during pre-implant injection when the silicone travels from injector system 400 through a gas/liquid check valve of surgical instrument 100 that is releasably connected with port 92. In some embodiments, the gas/liquid check valve is releasably connected with port 92 and/or other components of expandable implant 12 in an in-vivo quick release configuration. In some embodiments, the quick release connection of the gas/liquid check valve with port 92 facilitates subcutaneous release and/or detachment in-vivo of the components during employment of spinal implant system 10, for example, using a percutaneous approach. In some embodiments, the gas/liquid check valve includes a female mating element and port 92 includes a male mating element of the in-vivo quick release configuration. In some embodiments, the gas/liquid check valve includes a male mating element and port 92 includes a female mating element of the in-vivo quick release configuration. In some embodiments, the mating elements include detents, spring biased fingers, luer lock, clips, key/keyslot, adhesive, dovetail, friction fit and/or pressure fit. In some embodiments, the mating elements include internal and external locking features between the female and male connectors that resist and/or prevent pull forces to separate the connectors when circumferentially constrained. See also, the examples and disclosure of systems, surgical instruments, connectors, valves and methods shown and described in U.S. patent application Ser. No. 14/667,383 filed Mar. 24, 2015, and published as U.S. Patent Application Publication No. 20160278822, on Sep. 29, 2016, the entire contents of which being incorporated herein by reference.

Body 14 is expanded in vivo to a selected configuration such that body 14 is disposed with space S, and spinous process SP1 is disposed with cavity 70 and spinous process SP2 is disposed with cavity 80, as shown in FIGS. 14 and 15. Surface 32a engages spinous process SP1 and surface 32b engages spinous process SP2. The silicone disposed with body 14 in vivo is cured to harden implant 12 in the selected expanded configuration, as shown in FIG. 15. In some embodiments, body 14 expands in the cranial-caudal direction for distraction of spinous process SP1 and spinous process SP2. In some embodiments, expansion of body 14 is restricted in the anterior direction and the posterior direction to facilitate distraction of vertebrae V. In some embodiments, expansion of body 14 is restricted to resist and/or prevent impingement on the spinal canal of vertebrae V.

In some embodiments, spinal implant system 10 includes an agent, which may be disposed, packed, coated or layered within, on, adjacent or about the components and/or surfaces of spinal implant system 10, and/or disposed with tissue. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member including a body and an actuator, the body including a port that is connectable with a pressurized fluid source, the actuator comprising a handle having a threaded inner surface and a screw positioned within the handle such that a threaded outer surface of the screw engages the threaded inner surface;
   a second member comprising a first end that is positioned within the screw and a second end that includes a cavity, the first end being fixed to the screw; and an implant configured to be positioned in the cavity, the implant being disposable between a contracted configuration and an expanded configuration, wherein the handle is rotatable relative to the screw for selective translation of the second member relative to the body.

2. A surgical instrument as recited in claim 1, wherein the second member is adjustable relative to the first member in a first axial direction and a second, opposing axial direction via the actuator.

3. A surgical instrument as recited in claim 1, wherein the body includes a mixing chamber.

4. A surgical instrument as recited in claim 1, wherein the body defines a longitudinal axis and includes a mixing chamber disposed in axial alignment therewith.

5. A surgical instrument as recited in claim 1, wherein the second member includes an outer cannula and a filling tube positioned within the cannula, the cannula having an outer surface that directly engages an inner surface of the screw.

6. A surgical instrument as recited in claim 1, further comprising the fluid source, wherein the fluid source is detachably connected with the body.

7. A surgical instrument as recited in claim 1, further comprising the fluid source, wherein the fluid source includes an in vivo curable material.

8. A surgical instrument as recited in claim 1, wherein the first end includes an outer surface having a pressure fit connection with an inner surface of the screw.

9. A surgical instrument as recited in claim 1, wherein the second member includes an outer cannula and a filling tube positioned within the cannula, the cannula having an outer surface that directly engages an inner surface of the screw, the filling tube having an outer surface that directly engages an inner surface of the body.

10. A surgical instrument as recited in claim 1, wherein the second member includes an outer cannula and a filling tube positioned within the cannula, the cannula having a proximal end that is positioned between opposite proximal and distal ends of the filling tube.

11. A surgical instrument as recited in claim 1, wherein the implant includes a body comprising an intermediate portion having a baffle to regulate the flow of the injectable material and provide an expansion limit surface of the body of the implant.

12. A surgical instrument as recited in claim 1, wherein the implant includes a body manufactured from a porous fabric material, an outer surface of the body of the implant being coated with a non-permeable material to coat the porous material.

13. A surgical instrument comprising:
a rotatable handle being connectable with a pressurized fluid source including an in vivo curable material;
a tubular screw engaged with the handle such that a threaded outer surface of the screw engages a threaded inner surface of the handle;
a member connected with the handle and the fluid source, the member comprising a first end that is positioned within the screw and a second end that includes a cavity, the first end being fixed to the screw; and
an implant configured to be positioned in the cavity, the implant being disposable between a contracted configuration and an expanded configuration,
wherein the handle is rotatable relative to the screw for selective translation of the member relative to the handle.

14. A surgical system comprising:
an access cannula;
a trocar with a rigid tip, the trocar being disposable with the cannula; and
a surgical instrument disposable with the cannula and including a body and an actuator, the body including a port that is connectable with a pressurized fluid source, the actuator comprising a handle having a threaded inner surface and a screw positioned within the handle such that a threaded outer surface of the screw engages the threaded inner surface, the first end being fixed to the screw, the surgical instrument further including a second member comprising a first end that is positioned within the screw and a second end defining a cavity configured for disposal of an expandable implant, the handle being rotatable relative to the screw for selective translation of the second member relative to the body of the first member.

15. A surgical system as recited in claim 14, wherein the cannula includes a curvature.

16. A surgical system as recited in claim 14, wherein the trocar includes a flexible shaft.

17. A surgical system as recited in claim 14, wherein the trocar includes a pistol grip handle.

18. A surgical system as recited in claim 14, further comprising a pressurized fluid source connected with the body.

19. A surgical system as recited in claim 18, wherein the fluid source includes an in vivo curable material.

20. A surgical system as recited in claim 14, wherein the body defines a longitudinal axis and includes a mixing chamber disposed in axial alignment therewith.

* * * * *